United States Patent [19]
Vora

[11] Patent Number: 5,300,715
[45] Date of Patent: Apr. 5, 1994

[54] OLEFIN PROCESS WITH REMOVAL OF AROMATIC BY-PRODUCTS

[75] Inventor: Bipin V. Vora, Darien, Ill.

[73] Assignee: UOP, Des Plaines, Ill.

[21] Appl. No.: 958,842

[22] Filed: Oct. 9, 1992

[51] Int. Cl.[5] ............................................. C07C 5/00
[52] U.S. Cl. ................................. 585/254; 585/500; 585/654; 585/655; 585/804; 585/809; 585/820; 585/319; 585/322; 585/324
[58] Field of Search ................ 585/500, 654, 655, 804, 585/809, 820, 319, 254, 322, 324

[56] References Cited
U.S. PATENT DOCUMENTS 4,523,045  6/1985  Vora ..................................... 585/254

Primary Examiner—Patrick P. Garvin
Assistant Examiner—E. D. Irzinski
Attorney, Agent, or Firm—Thomas K. McBride; John G. Tolomei

[57] ABSTRACT

An improved process for the production of linear olefinic hydrocarbons by paraffin dehydrogenation and adsorptive separation is disclosed. Aromatic by-products normally formed in paraffin dehydrogenation are selectively removed using at least one aromatics removal zone. Removal of these aromatic by-products significantly increases the purity of the olefinic hydrocarbon product and increases the capacity of the adsorptive separation zone. The improved process is believed to increase the life of the adsorbent in the adsorptive separation zone and the life of the catalyst in the dehydrogenation zone.

23 Claims, 2 Drawing Sheets

OLEFIN PROCESS WITH REMOVAL OF AROMATIC BY-PRODUCTS

FIELD OF THE INVENTION

The invention relates to the broad field of hydrocarbon processing. The invention may also be broadly classified as relating to a combination process for the production of olefinic hydrocarbons. More specifically, the invention relates to a hydrocarbon conversion process for the catalytic dehydrogenation of acyclic paraffinic hydrocarbons to produce monoolefinic hydrocarbons. The subject process also includes a selective aromatics removal step to eliminate aromatic hydrocarbons, the adsorptive separation of olefins, and the recycling of unconverted paraffins. The selective aromatics removal removes aromatic by-products present in the dehydrogenation reactor effluent stream.

BACKGROUND OF THE INVENTION

The production of acyclic olefinic hydrocarbons by dehydrogenation is a highly useful hydrocarbon conversion process. The product olefinic hydrocarbons find utility in the production of a wide variety of useful chemicals including synthetic lubricants, detergents, polymers, alcohols, plasticizers, etc.

Modern catalytic dehydrogenation processes provide a high degree of selectivity to the formation of linear monoolefins. However, they are still troubled by the production of by-products, basically due to thermal cracking reactions and to undesired catalytic dehydrogenation side reactions. The by-products fall into three broad classes, light hydrocarbons formed by cracking reactions, diolefinic hydrocarbons having the same carbon number as the desired monoolefinic hydrocarbons, and aromatic hydrocarbons also having the same carbon number as the desired monoolefinic hydrocarbons. The production of aromatic hydrocarbons is most troublesome, especially when the objective is to produce high purity monoolefinic hydrocarbons. The light hydrocarbons which result from cracking reactions can normally be readily removed from the dehydrogenation effluent stream by a relatively easy fractional distillation step. The diolefinic hydrocarbons which result from dehydrogenation reactions can normally be readily converted to monoolefinic hydrocarbons in the dehydrogenation effluent product stream by a relatively easy catalytic selective hydrogenation step. In contrast, the aromatic hydrocarbons remain in the dehydrogenation effluent stream. The presence of aromatic by-products in an olefinic product stream is often undesirable because the aromatic hydrocarbons are impurities that react in downstream processes to form different compounds than the monoolefinic hydrocarbons.

It is well known that aromatic by-products are formed during the catalytic dehydrogenation of paraffins. For instance, the article starting at page 86 of the Jan. 26, 1970, issue of "Chemical Engineering" states that the product of the dehydrogenation of linear paraffins includes aromatic compounds. The nature of the particular aromatic by-products that are formed in dehydrogenation is not essential to this invention. Without limiting this invention in any way, these aromatic by-products are believed to include, for example, alkylated benzenes, naphthalenes, other polynuclear aromatics, alkylated polynuclear hydrocarbons in the $C_{10}$–$C_{15}$ range, indanes and tetralins, that is, they are aromatics of the same carbon number as the paraffin being dehydrogenated and may be viewed as aromatized normal paraffins. The particular side reactions that lead to the formation of the aromatic by-products are also not essential to this invention. Again, without limiting this invention in any way, an illustration of some of the parallel thermal cracking reactions that can lead to the formation of aromatic by-products is found in the diagram at the top of page 4–37 of the book edited by R. A. Meyers entitled "Handbook of Petroleum Refining Processes" (McGraw Hill, N.Y., 1986). Typically, from about 1.0 to about 7.0 weight percent, and generally to the extent of no more than 10.0 weight percent, of the converted feed paraffinic compounds of a dehydrogenation zone form aromatic by-products. Although some commercially available dehydrogenation catalysts are more selective than others at minimizing the formation of aromatic by-products, it is believed that these by-products are formed, at least to a small extent, at suitable dehydrogenation conditions in the presence of most, if not all, commercially-available dehydrogenation catalysts. Since it is an economic advantage to operate the dehydrogenation zone at conditions that produce a high conversion of the feed paraffinic compounds and a high yield of the desired olefins, these aromatic by-products are produced, at least to a small extent, in most if not all commercial dehydrogenation zones.

INFORMATION DISCLOSURE

Processes for the production of monoolefinic hydrocarbons from acyclic paraffinic hydrocarbons are well known to those skilled in the hydrocarbon conversion arts. Such processes are operated commercially in petroleum refineries and petrochemical plants. A flow diagram of a process for the production of monoolefinic hydrocarbons is taught in U.S. Pat. No. 4,523,045 issued to Vora.

BRIEF SUMMARY OF THE INVENTION

The invention provides an improved process for the production of linear monoolefinic hydrocarbons from linear paraffinic hydrocarbons. The improved results are obtained through the use of a selective aromatics removal zone which removes aromatic by-products present in the net product of the dehydrogenation zone. This increases the purity of the monoolefin product stream and increases the capacity of the monoolefin adsorptive separation zone. In addition, it is believed to increase the life of the adsorbent in the monoolefin adsorptive separation zone.

In an integrated process, such as the subject process in which the aromatic by-products are passed to a monoolefin separation zone, almost half of the aromatic by-products that enter into the monoolefin separation zone adsorb onto sites of the adsorbent that are normally occupied by monoolefinic hydrocarbons. This results in a direct decrease in the capacity of the adsorbent for adsorption of monoolefinic hydrocarbons and, consequently, a decreased rate of production of monoolefinic hydrocarbons compared to when aromatic compounds are not passed to the monoolefin separation zone. More specifically, the passing of aromatic hydrocarbons to the monoolefin separation zone directly reduces production rates of monoolefinic hydrocarbons by 5 percent or more in such an integrated process. Furthermore, since most of the aromatic by-products are desorbed from the adsorbent sites when the monoolefinic hydrocarbons are desorbed, the aromatic by-products contaminate the monoolefinic product, thereby decreasing the value of the product. Therefore, the presence of aromatic by-products in the feed to a monoolefin separation zone decreases the rate of monoolefin production and also contaminates the monoolefin product. In addition, since some of the aromatic by-products are believed to be more difficult to desorb from the adsorbent than the monoolefinic hydrocarbons, aromatic by-products may build up on the sites of the adsorbent, thereby causing the selectivity and capacity of the desorbent to deteriorate over time due to the accumulation of aromatic foulants on the adsorbent.

The presence of aromatic by-products in an integrated process, such as the subject process in which a paraffin-rich material is recycled to the dehydrogenation zone, may present an additional problem. This problem is an increased rate of dehydrogenation catalyst deactivation compared to when feed boiling range unsaturated hydrocarbons derived from the dehydrogenation reactor effluent are not returned to the dehydrogenation reactor. It is estimated that almost half of the aromatic by-products that enter into the monoolefin separation zone are returned to the dehydrogenation zone. More specifically, the return of unsaturated hydrocarbons including aromatic by-products to the dehydrogenation zone inlet has been associated with catalyst lives being reduced by 30 percent or more. It is believed that selective aromatics removal will reduce the increased dehydrogenation catalyst deactivation observed when unsaturated hydrocarbons are recycled from the separation zone. This is based on the observation that recycling to the dehydrogenation zone of highly unsaturated hydrocarbons such as linear alkylated benzenes or even much less unsaturated hydrocarbons such as monoolefins significantly reduces dehydrogenation catalyst life. The explanation for this is that the presence of unsaturated aromatics or other unsaturated aromatic hydrocarbons at the inlet of the catalyst bed in part promotes coke deposition and catalyst deactivation. In a nonrecycle or aromatic-free recycle dehydrogenation process, aromatic hydrocarbons are rapidly removed from the catalyst bed due to the high space velocities normally employed in dehydrogenation reactors. Further, it is believed that it is necessary to first dehydrogenate a paraffin to a monoolefin before any aromatics are produced. The production of aromatics is, therefore, greatest at the near equilibrium conditions at the exit of a non-recycle reactor, and most of the catalyst bed is accordingly spared severe deactivation by coke formation. Coke formation is believed to follow the production of polymeric or cyclic "coke precursors" which are derived from the aromatics. The rapid removal of aromatics from the reaction zone coupled with their formation in the later stages of the dehydrogenation reaction tends to minimize coke formation on the catalyst. In comparison, the recycling of aromatics to the reactor tends to promote coke deposition and catalyst deactivation. The aromatics are then present in the entire catalyst bed and the whole bed is subjected to deactivation. The subject invention greatly reduces or eliminates the presence of aromatics in the charge stream of the dehydrogenation reactor, thereby significantly lengthening dehydrogenation catalyst life.

The invention is an improved process for the production of monoolefinic hydrocarbons that eliminates or significantly reduces the aromatic by-products in the feedstock to the monoolefin separation zone by the selective removal of aromatic hydrocarbons from one or more locations in the process. This process has a number of advantages over prior art processes, including the previously cited U.S. Pat. No. 4,523,045. For instance, this reference process does not prevent aromatic by-products from entering the monoolefin separation zone. The olefin-rich product stream of the reference is therefore contaminated by a higher aromatic by-product concentration than the product stream of the subject invention. A second disadvantage of the reference process is that some aromatic by-products present in the recycle stream are passed to the dehydrogenation zone.

Accordingly, it is an objective of the subject invention to provide an improved process for converting linear paraffins to linear monoolefinic hydrocarbons. It is an objective of this invention to increase the purity of the monoolefinic hydrocarbon product. It is another objective of the invention to increase the capacity of the monoolefin separation zone employed in an integrated dehydrogenation-separation process for the production of linear monoolefinics. It is a further objective of this invention to reduce the fouling of adsorption sites on the adsorbent in the monoolefin separation zone and to thereby increase the effective life of the adsorbent. It is an additional objective of this invention to increase the life of dehydrogenation catalyst employed in an integrated dehydrogenation-separation process for the production of linear monoolefins.

The present invention has three embodiments. One broad embodiment of the present invention may be characterized as a process for the production of aliphatic monoolefinic hydrocarbons. A feed stream, which comprises at least one $C_4$ to $C_{20}$ feed paraffinic hydrocarbon, passes into a dehydrogenation zone to dehydrogenate the entering paraffinic hydrocarbons to monoolefinic hydrocarbons. A dehydrogenation zone effluent stream, which comprises feed paraffinic hydrocarbons, light hydrocarbons, aromatic by-products, and monoolefinic hydrocarbons corresponding to the feed paraffinic hydrocarbon, is recovered from the dehydrogenation zone. The dehydrogenation zone effluent stream passes into a stripping zone to strip the entering light hydrocarbons, and a stripped dehydrogenation zone effluent stream comprising feed paraffinic hydrocarbons and monoolefinic hydrocarbons is recovered from the stripping zone. The stripped dehydrogenation zone effluent stream passes into a monoolefin separation zone to concentrate the entering monoolefinic hydrocarbons into a product stream having a first concentration of monoolefinic hydrocarbon that is recovered from the monoolefin separation zone and withdrawn from the process. A monoolefin separation zone effluent stream having a second concentration of monoolefinic hydrocarbon that is less than the first concentration is recovered from the monoolefin separation zone and at least a portion of the monoolefin separation zone effluent stream is recycled to the dehydrogenation zone. In this process, at least a portion of the aromatic by-products are removed from at least one of the dehydrogenation zone effluent stream, the stripped dehydrogenation zone effluent stream, and the monoolefin separation zone effluent stream. The aromatic by-products are removed in at least one aromatics removal zone that operates at removal conditions effective to selectively remove the aromatic by-products and reduce the concentration of aromatic by-products in the stripped dehydrogenation zone effluent stream to a level of no more than about 0.5 weight percent.

A more limited embodiment of the present invention may be characterized as a process for the production of aliphatic monoolefinic hydrocarbons. A feed stream, which comprises at least one $C_4$ to $C_{20}$ feed paraffinic hydrocarbon, passes into a dehydrogenation zone to dehydrogenate the entering paraffinic hydrocarbons to monoolefinic hydrocarbons. A dehydrogenation zone effluent stream, which comprises feed paraffinic hydrocarbons, light hydrocarbons, aromatic by-products, and monoolefinic hydrocarbons corresponding to the feed paraffinic hydrocarbon, is recovered from the dehydrogenation zone. The dehydrogenation zone effluent stream passes into a stripping zone to strip the entering light hydrocarbons, and a stripped dehydrogenation zone effluent stream comprising feed paraffinic hydrocarbons, aromatic by-products, and monoolefinic hydrocarbons is recovered from the stripping zone. The stripped dehydrogenation zone effluent stream passes into a monoolefin separation zone to concentrate the entering monoolefinic hydrocarbons into a product stream having a first concentration of monoolefinic hydrocarbon that is recovered from the monoolefin separation zone. A monoolefin separation zone effluent stream having a second concentration of monoolefinic hydrocarbon that is less than the first concentration is recovered from the monoolefin separation zone and at least a portion of the monoolefin separation zone effluent stream is recycled to the dehydrogenation zone. The product stream passes into at least one aromatics sorptive separation zone containing a sorbent to selectively remove at least a portion of the aromatic by-products in the product stream. An aromatics removal zone effluent stream having a concentration of aromatic by-products no more than about 0.5 weight percent is recovered from the aromatics removal zone and withdrawn from the process. The sorbent is regenerated to desorb aromatic by-products by contacting the sorbent and a regenerant stream comprising benzene at regeneration conditions. A regeneration effluent stream comprising benzene and monoolefinic hydrocarbons is produced during regeneration and passed into a regenerant separation zone to separate the entering hydrocarbons into a first stream comprising benzene and a second stream comprising the monoolefinic hydrocarbons. At least a portion of the first stream forms at least a portion of the regenerant stream.

A particular embodiment of the present invention may be characterized as a process for the production of aliphatic monoolefinic hydrocarbons. A feed stream, which comprises at least two different $C_6$-plus feed paraffinic hydrocarbons, passes into a catalytic paraffin dehydrogenation zone to dehydrogenate paraffinic hydrocarbons to monoolefinic hydrocarbons. A hydrogen-rich gas stream and a liquid-phase effluent stream are recovered from the dehydrogenation zone. The liquid-phase effluent stream, which comprises feed paraffinic hydrocarbons, light hydrocarbons, aromatic by-products, and monoolefinic and diolefinic hydrocarbons corresponding in carbon number to the feed paraffinic hydrocarbons, passes into a selective hydrogenation zone to convert the diolefinic hydrocarbons to monoolefinic hydrocarbons. A selective hydrogenation zone effluent stream comprising light hydrocarbons, aromatic by-products, feed paraffinic hydrocarbons, and monoolefinic hydrocarbons is recovered from the selective hydrogenation zone. The selective hydrogenation zone effluent stream passes into a fractionation zone to remove the entering dissolved hydrogen and light hydrocarbons, and a stripped selective hydrogenation zone effluent stream comprising feed paraffinic hydrocarbons and monoolefinic hydrocarbons is recovered from the fractionation zone. The stripped selective hydrogenation zone effluent stream passes into at least one aromatics removal zone to selectively remove the aromatic by-products from the stripped selective hydrogenation zone effluent stream and reduce the concentration of aromatics by-products in the stripped selective hydrogenation zone effluent stream to a level no more than about 0.5 weight percent. The aromatics removal zone contains a 13X zeolite sorbent and operates at conditions including a temperature of from about 20° to about 300° C. and a liquid hourly space velocity of from about 1 to about 10 $hr^{-1}$. An aromatics removal zone effluent stream that comprises paraffinic hydrocarbons and monoolefinic hydrocarbons is recovered from the aromatics removal zone. The aromatics removal zone effluent stream contacts a solid adsorbent in a monoolefin adsorptive separation zone to separate the entering monoolefinic hydrocarbons into a product stream and a monoolefin separation zone effluent stream. The product stream is recovered from the monoolefin separation zone and withdrawn from the process. The monoolefin separation zone effluent stream, which has a concentration of monoolefinic hydrocarbon of from about 0.5 to about 2.0 mol percent is recovered from the monoolefin separation zone and is recycled to the dehydrogenation zone.

Other embodiments, purposes, and objectives will become clear from the ensuing discussion.

DETAILED DESCRIPTION OF THE INVENTION

Figure 1:
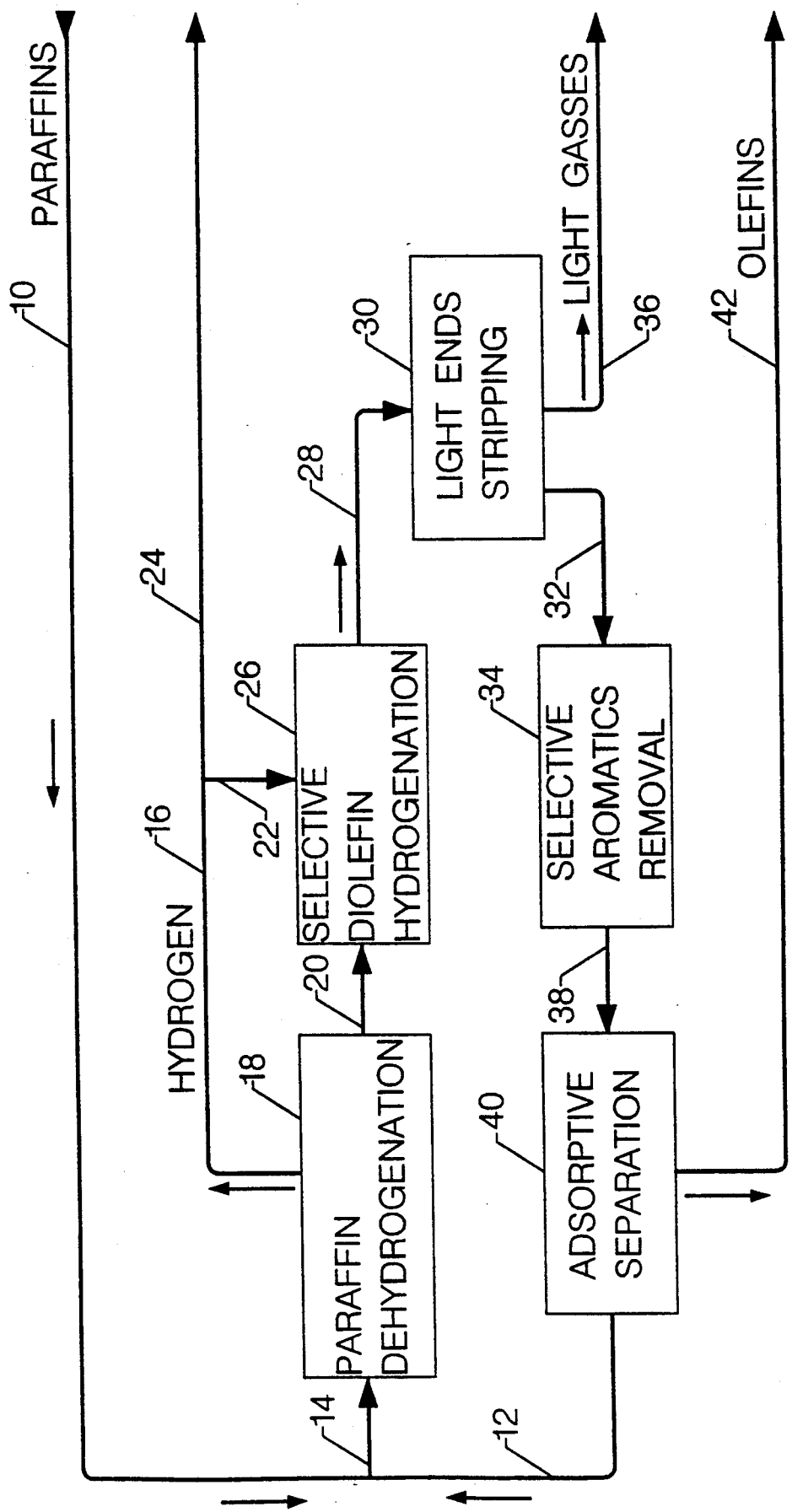
FIG. 1 is a simplified process flow diagram of a preferred embodiment of the invention where the aromatics removal zone is located between the stripping zone and the monoolefin adsorptive separation zone.

The feed hydrocarbon charged to the subject process is a $C_4$-plus normal paraffin. Paraffins which contain six or more carbon atoms per molecule are preferred over $C_4$ and $C_5$ paraffins. The upper limit on the carbon number of the charge stock is basically set by the volatility and processability of the charge stock in the dehydrogenation reactor. This upper limit is at about $C_{22}$ paraffins. The feed stream may be a high purity stream of a single paraffin or the feed stream may comprise a mixture of two or more paraffins having different carbon numbers. For instance, an admixture of $C_{10}$ to $C_{15}$ normal paraffins is often passed through a dehydrogenation zone to produce linear olefins which are consumed in the production of linear alkylbenzenes suitable for use in the production of biodegradable detergents. It is normally preferred that the feed stream contains a series of paraffins having a carbon number range of four or more. Adsorptive separation is highly suited to preparing such mixtures.

Conventional equipment and process flows can be used in the dehydrogenation zone. In this arrangement, a fresh paraffinic hydrocarbon feed stream and a recycle stream containing paraffins from a monoolefin separation zone are combined with recycled hydrogen. This forms a reactant stream which is heated by indirect heat exchange and is then passed through a bed of a suitable catalyst maintained at the proper dehydrogenation conditions of temperature, pressure, etc.

The dehydrogenation reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by the reference to U.S. Pat. Nos. 3,647,680; 3,706,536; 3,825,116; 3,839,196; 3,839,197; 3,854,887; 3,856,662; and 3,978,150.

The particular dehydrogenation conditions employed within the reaction zone may vary depending on such factors as the catalyst activity, feed carbon number, and the desired conversion. The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. What is important is that catalysts for dehydrogenation are well known to those skilled in the dehydrogenation art and need not be described here in great detail. We emphasize that the nature of the dehydrogenation catalyst is not critical to the success of our invention and is largely a matter of choice to be made by the practitioner.

The effluent of this dehydrogenation catalyst bed or reactor effluent stream is cooled and partially condensed and passed into a vapor-liquid separation zone. Part of the uncondensed material is employed as the hydrogen-rich recycle gas stream. The remainder of the uncondensed hydrogen-rich material is the net production of hydrogen which may be used in other applications such as desulfurization. As used herein, the term "rich" is intended to indicate a molar concentration of the indicated compound or class of compounds above 50%. The vapor-liquid separation zone also produces a liquid-phase effluent stream. This stream is basically an admixture of dehydrogenated and undehydrogenated acyclic hydrocarbons and aromatic hydrocarbons. The dehydrogenated acyclic hydrocarbons and the aromatic by-products generally have the same carbon numbers as the corresponding feed hydrocarbons. This liquid-phase effluent stream will also contain some dissolved hydrogen and light hydrocarbons produced by various cracking reactions which occur at the high temperatures employed in the dehydrogenation reactor and heaters.

In a particular application of the subject process, the liquid phase process stream withdrawn from this separation zone is passed into a selective hydrogenation reaction zone. However, a selective hydrogenation zone is not an essential feature of the present invention. Where present, this reaction zone contains a selective hydrogenation catalyst and is maintained at conditions necessary for selective hydrogenation of diolefins to monoolefins. The placement of the selective hydrogenation zone at this point makes it very economical to perform the desired selective hydrogenation. One reason for this is that the reactants are in the desired liquid phase state as they leave the vapor-liquid separation zone. A second reason is that the temperature of the liquid-phase effluent stream as it leaves the separation zone will normally be within the desired operating range of the selective hydrogenation reaction zone.

Where the selective hydrogenation zone is present at the point in the process described above, the effluent of the selective hydrogenation zone is a liquid phase stream similar in nature to the liquid-phase effluent stream removed from the separator of the dehydrogenation zone but having a reduced concentration of diolefinic hydrocarbons and a corresponding increase in the concentration of monoolefinic hydrocarbons. In one embodiment of this invention this selective hydrogenation zone effluent stream, where present, is passed into a stripping column designed and operated to remove overhead all compounds which are more volatile than the lightest hydrocarbon which it is desired to have present in the net effluent stream of the hydrogenation process. These lighter materials will be concentrated into a net overhead stream which will comprise an admixture of hydrogen and light hydrocarbons. The purpose of the stripping operation is to prevent the entrance of volatile light materials into downstream processing zones where they could present certain operational problems. The stripping column also serves to eliminate the light hydrocarbons from the recycle stream which returns paraffinic hydrocarbons to the dehydrogenation zone from the downstream separation zone. The recycling of light hydrocarbons to the dehydrogenation zone is not desired as it normally has an adverse impact on the dehydrogenation catalyst. The stripping column can also be operated to adjust the initial boiling point or composition of the downstream adsorptive separation zone.

In one embodiment of the present invention, the stripped selective hydrogenation zone effluent stream is passed into an aromatics removal zone. The majority of this description is presented in terms of locating the aromatics removal zone to remove the aromatic by-products from the stripped selective hydrogenation zone effluent stream since this is a preferred embodiment. However, this description is not intended to limit the scope of the invention in any way. In actuality, the invention achieves the objectives set forth above by selectively removing at least a portion of the aromatic by-products in the dehydrogenation zone effluent stream using at least one aromatics removal zone placed in one or more locations in the prior art processes. For example, in another embodiment, the aromatic by-products may be selectively removed from the selective hydrogenation zone effluent stream. In a third embodiment, where the bottoms liquid stream of the extract column in the monoolefin separation zone is recycled to the dehydrogenation zone, which is normally the case in commercial applications, the aromatic by-products may be selectively removed from the recycle stream. In a fourth embodiment, where the subject process does not include a selective hydrogenation zone, the aromatic by-products may be selectively removed from the dehydrogenation zone effluent stream. In yet another embodiment, the aromatic by-products may be selectively removed from the product stream of the monoolefin separation zone. These locations set forth above are not necessarily equivalent in terms of the required equipment, such as heaters, heat exchangers, vessels, coolers, and etc., to practice our invention. Those skilled in the art of hydrocarbon processing are able to design and provide the required equipment.

The aromatics removal zone is preferably located between the dehydrogenation zone and the monoolefin separation zone because the aromatic by-products are preferably selectively removed prior to entering the monoolefin separation zone. When the aromatic by-products from the dehydrogenation section enter the monoolefin separation zone, several possibilities can then occur. First, some of the aromatic by-products are adsorbed onto adsorption sites on the adsorbent and, as previously mentioned, are subsequently desorbed with the monoolefinic hydrocarbons thereby contaminating the monoolefin product stream. Second, as mentioned above, some of the aromatic by-products are adsorbed onto adsorption sites on the adsorbent and are not desorbed with the monoolefinic hydrocarbons. These aromatic by-products accumulate on the adsorbent and may decrease the effective life of the adsorbent. Third, some of the aromatic by-products pass with the paraffinic hydrocarbons through the monoolefin separation zone unadsorbed, are recovered with the bottoms liquid stream of the extract column of the monoolefin separation zone which is recycled to the dehydrogenation zone, and ultimately accumulate to unacceptable concentrations in the process. In the prior art processes the concentration of aromatic by-products in the stripped selective hydrogenation zone effluent stream can typically accumulate to 0.5-2.0 weight percent. One embodiment in accord with the invention is to remove at least a portion of the aromatic by-products in the stripped dehydrogenation zone effluent stream to reduce the concentration of the aromatic by-products in the stripped dehydrogenation zone effluent stream to less than 0.5 weight percent aromatic by-products. In a more specific embodiment, the concentration of aromatic by-products is reduced to less than about 0.2 weight percent. In a more specific embodiment, the concentration of aromatic by-products is reduced to less than about 0.1 weight percent. Although it would be desirable to remove the aromatic by-products in the product recovery section of the monoolefin separation zone, the difficulty of separating the aromatic by-products from not only the desorbed monoolefins, but also the unadsorbed paraffins all of the same carbon number precludes such an arrangement.

Suitable aromatics removal zones may be selected from any processing methods which exhibit the primary requirement of selectivity for removing the aromatic by-products. Suitable aromatics removal zones include, for example, aromatics sorptive separation zones and liquid-liquid extraction zones. However, it should be recognized that a particular aromatics removal zone may give better results than another zone. The preferred aromatics removal zone is an aromatics sorptive separation zone.

Where the aromatics removal zone is an aromatics sorptive separation zone, the subject invention can be practiced in fixed bed or moving sorbent bed systems, but the fixed bed system is preferred. The sorbent may be installed in one or more vessels and in either series or parallel flow. The flow of the stream containing the aromatic by-products through the aromatics sorptive separation zone is preferably performed in a parallel manner so that when one of the sorbent beds or chambers is spent by the accumulation of the aromatic by-products thereon, the spent zone may be by-passed while continuing uninterrupted operation through the parallel zone. The spent zone of sorbent may then be regenerated or the spent sorbent may be replaced as desired.

The subject invention may also be practiced in a concurrent, pulsed batch process, like that described in U.S. Pat. No. 4,159,284 or in a concurrent, pulsed continuous process, like that disclosed in U.S. Pat. Nos. 4,402,832 and 4,478,721, both issued to Gerhold.

The subject invention may also be practiced in a countercurrent simulated moving bed system, such as described in U.S. Pat. No. 2,985,589 issued to Broughton. Cyclic advancement of the input and output streams can be accomplished by manifolding systems, which are also known, e.g., by rotary disc valves shown in U.S. Pat. Nos. 3,040,777 and 3,422,848. Equipment utilizing these principles are familiar, in sizes ranging from pilot plant scale, such as described in U.S. Pat. No. 3,706,812 issued to deRosset, to commercial scale in flow rates from a few cc per hour to many thousands of gallons per hour.

Suitable sorbents may be selected from materials which exhibit the primary requirement of selectivity for the aromatic by-products and which are otherwise convenient to use. Suitable sorbents include, for example, molecular sieves, silica, activated carbon, activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic by-products, the selectivity of the sorbent to retain the aromatic by-products which are more detrimental to solid alkylation catalysts, and the cost of the sorbent. The preferred sorbent is a molecular sieve, and the preferred molecular sieve is 13X zeolite (sodium zeolite X). Detailed descriptions of zeolites may be found in the book authored by D. W. Breck entitled "Zeolite Molecular Sieves" published by John Wiley and Sons, New York, in 1974.

Those skilled in the art are able to select the appropriate conditions for operation of the sorbent without undue experimentation. For example, a fixed bed aromatics sorptive separation zone containing 13X zeolite may be maintained at a temperature from about 20° C. to about 300° C. and preferably from about 100° C. to about 200° C., a pressure effective to maintain the stream containing the aromatic by-products in a liquid phase at the chosen temperature, and a liquid hourly space velocity from about 1 $hr^{-1}$ to about 10 $hr^{-1}$ and preferably from about 1 $hr^{-1}$ to about 3 $hr^{-1}$. The flow of the stream containing the aromatic by-products through the aromatics sorptive separation zone may be conducted in an upflow, downflow or radial-flow manner.

Although both liquid and vapor phase operations can be used in many sorptive separation processes, liquid phase operation is preferred for the aromatics sorptive separation zone of the present invention because of the lower temperature requirements and because of the higher sorption yields of the aromatic by-products that can be obtained with liquid phase operation over those obtained with vapor phase operation. Therefore, the temperature and pressure of the aromatics sorptive separation zone during sorption of the aromatic by-products are preferably selected to maintain in a liquid phase the stream from which the aromatic by-products are selectively removed. Alternatively, the temperature and pressure of the aromatics sorptive separation zone during sorption of the aromatic by-products can be selected to maintain in a liquid phase the aromatic by-products in the stream from which the aromatic by-products are selectively removed. Mixed phases (i.e., a combination of a liquid phase and a vapor phase) for the stream from which the aromatic by-products are separated are generally not preferred because of the well-known difficulties involved in maintaining uniform flow distribution of both a liquid phase and a vapor phase through a sorptive separation zone. However, the operating conditions of an aromatics sorptive separation zone can be optimized by those skilled in the art to operate over wide ranges, which are expected to include the conditions in the reaction zones of the invention and its variants. Therefore, an embodiment of the invention includes an aromatics sorptive separation zone contained in a common vessel with the dehydrogenation zone, the selective hydrogenation zone, where present, or the selective monoolefin hydrogenation zone.

Following an appropriate processing period which will depend on the composition of the stream containing the aromatic by-products and the particular aromatic by-products themselves, it is usually necessary to regenerate the sorbent, that is to remove the sorbed aromatic by-products from the sorbent so that the sorbent may be reused. There are numerous methods of regenerating the sorbent. It is not intended to limit this invention to any particular method of regenerating the sorbent. Any suitable regeneration method may be used. In a preferred method of regeneration, a wash of liquid benzene at desorbing conditions of temperature and pressure may be used.

It should be understood that in certain methods of regeneration it is also necessary to remove the regenerating medium from the sorbent before normal processing is resumed. This is particularly true if benzene has been employed to displace the sorbed aromatic by-products. This is because benzene is strongly adsorbed and, therefore, detrimental to some adsorbents that are employed in commercial monoolefin separation zones. The benzene that is present in the aromatics sorptive separation zone after regeneration may be conveniently removed from the sorbent by displacement, e.g., by passing a stream of the normal feed through the aromatics sorptive separation zone. The benzene is separated by fractionation from the normal feed without any special measures and recovered for reuse in regeneration.

It should be noted that the locations for the aromatics removal zone that were set forth above are not necessarily equivalent in terms of the required equipment for recovering the regenerating medium from the sorbent in an aromatics sorptive separation zone when normal processing is resumed. In one location, where the aromatics removal zone is located downstream of the selective hydrogenation zone and upstream of the stripping or fractionation zone, a regenerating medium that is lighter than the feed paraffinic hydrocarbons can be separated without any special measures from the aromatics removal zone effluent via the overhead of the stripping or fractionation zone. Such a regenerating medium that could be removed in this fashion upstream of the monoolefin separation zone is benzene. As an aromatic and in a manner similar to the aromatic by-products, some of the benzene that would enter the monoolefin separation zone would exit with the monoolefin product stream, thereby contaminating the product stream. Therefore, separating out the benzene upstream of the monoolefin separation zone helps to ensure that the benzene neither contaminates the product stream nor is detrimental to the adsorbent in the monoolefin separation zone. However, the disadvantage of recovering benzene in the overhead of the stripping zone is that it is recovered as a mixture with other $C_5-C_8$ light hydrocarbons from which it must be separated before it can be reused as a regenerating medium. In another location, where the aromatics removal zone is located on the stripped effluent stream downstream of the stripping or fractionation zone, a regenerating medium such as benzene that is lighter than the hydrocarbons in the stripped stream can be separated without any special measures in a regenerant fractionation zone upstream of the monoolefin separation zone. Although there is a cost associated with the additional fractionation zone, the advantage of recovering the regenerating medium in the overhead of a regenerant fractionation zone is that it is not recovered as a mixture with the light hydrocarbons that are stripped in the stripping zone, and therefore, it can be reused directly as a regenerating medium. This same advantage arises where the aromatics removal zone is located on the monoolefin product stream downstream of the monoolefin separation zone. Since this latter location of the aromatics removal zone does not result in the removal of the aromatic by-products prior to their entering the monoolefin separation zone, not all of the benefits associated with this invention will be realized in this embodiment. However, the advantages associated with ease of recovery of the regenerating medium may be a sufficient benefit in some applications to justify this location. Nevertheless, even in this latter location, the purity of the monoolefin product stream will be increased.

Those skilled in the art are able to select the appropriate conditions for regeneration of the sorbent without undue experimentation. For example, a fixed bed aromatics sorptive separation zone containing 13×zeolite may be regenerated using a desorbent mixture of 30 vol.% liquid benzene and 70 vol.% liquid decane at desorption conditions including a temperature from about 20° C. to about 300° C. and preferably from about 100° C. to about 200° C., a pressure of from atmospheric pressure to a pressure effective to maintain the desorbent mixture in a liquid phase at the chosen temperature, and a liquid hourly space velocity from about 1 $hr^{-1}$ to about 10 $hr^{-1}$ and preferably from about 1 $hr^{-1}$ to about 3 $hr^{-1}$. The flow direction of the desorbent mixture through the aromatics sorptive separation zone may be upflow or radial-flow, but the preferred direction is downflow. The phase of the desorbent mixture through the aromatics sorptive separation zone may be liquid phase, vapor phase, or a mixture of liquid and vapor phases.

Where the aromatics removal zone is a liquid-liquid extraction zone, the invention can be practiced by contacting the stream containing the aromatic by-products with a suitable solvent which selectively retains the aromatic by-products. Organic compounds suitable for use as part of the solvent composition include the aliphatic and cyclic alcohols, cyclic monomeric sulfones, the glycols and glycol ethers, as well as the glycol esters and glycol ether esters, but the preferred organic compound is a sulfolane. Typically, organic compounds belonging to the sulfolane class are 2-sulfolene, 2-methyl sulfolane, 2,3-dimethylsulfolane, 2,4-dimethyl-4-sulfolane, methyl-3-sulfonyl ether, ethyl-3-sulfonyl sulfide, and others. However, one of the disadvantages of these solvent systems is that most of these solvents also possess greater affinity to olefins with respect to paraffins, and as such, the aromatic extract will contain some olefinic hydrocarbons, which represents a loss of valuable product. The invention may be practiced using any conventional or convenient type of apparatus known to those skilled in the art. Also, the operating conditions suitable for the practice of the present invention are conventional. Generally, the amount of solvent composition utilized in admixture with an appropriate feedstock should be at least sufficient to dissolve the constituents to be extracted. It may be desirable to use a considerable excess over the theoretical amount of solvent composition necessary, especially when maximum purity and maximum recovery of aromatic by-products is required. Usually, in the extraction step, the solvent composition to feed ratios will range from about 1:1 to about 20:1 by volume, preferably from about 3:1 to about 15:1 by volume. A summary of the conditions necessary for the practice of the sulfolane type of solvent operation may be found in *Petroleum Refiner*, Volume 38, No. 9, September 1959, pages 185–192. Liquid-liquid extraction processes for removal and recovery of aromatic hydrocarbons from mixed hydrocarbon feeds are described in U.S. Pat. No. 3,433,735 issued to Broughton, U.S. Pat. No. 3,466,345 issued to De Graff and U.S. Pat. No. 3,642,614 issued to Van Tassel.

The effluent stream from the aromatics removal zone is passed to a monoolefin separation zone. The type of monoolefin separation zone used to recover the product olefins from the paraffin-olefin mixture is not a limiting characteristic of the subject process. Separatory techniques based upon liquid-liquid extraction or chemical binding can, therefore, be employed if they meet commercial standards of cost, effectiveness, and workability. It is greatly preferred that an absorptive type separation is employed, with the paraffin-olefin mixture being passed through a bed of a solid adsorbent which selectively collects either the olefins or the paraffins from the flowing stream. The selective retention of the olefins is preferred as there is a smaller quantity of olefins. This could be performed in a simple swing bed system with one or more beds being used to collect olefins while previously used beds are being regenerated as by the use of a desorbent, a temperature increase, a pressure decrease, or a combination of these commonly employed regeneration techniques. Another type of adsorptive separation process which may be employed is described in U.S. Pat. No. 4,402,832. This process simulates continuous concurrent movement of the adsorbent relative to the fluid flow.

A preferred configuration of the monoolefin adsorptive separation zone is described in U.S. Pat. Nos. 3,239,455; 3,617,504; 4,133,842. The use of this separatory technique to separate olefinic hydrocarbons from a paraffin-olefin mixture is the subject of U.S. Pat. Nos. 3,510,423; 3,720,604; 3,723,302; and 3,755,153. These references describe operating conditions and methods and suitable adsorbents. They also describe in some detail the use of a preferred technique for simulating countercurrent flow of the feed hydrocarbons and the adsorbent. A variation in the equipment used to perform this process is the subject of U.S. Pat. No. 4,434,051. Adsorptive separations can be performed using either vapor phase or liquid phase conditions within the adsorption zone. The use of liquid phase methods is preferred as it allows operation at lower temperatures, which minimizes any polymerization of olefins. Operating conditions for the adsorbent chambers can include a temperature of from about 25° to about 225° C. and a pressure of from about atmospheric to about 750 psig.

A monoolefin sorptive separation step can be practiced using any type of commercially operable and practical selective adsorbent. The adsorbent may, therefore, be a naturally-occurring substance or a man-made material and may be in the form of extrudates, pellets, spheres, etc. The adsorbent can be formed from charcoal, alumina, silica, or various clays, and mixtures of these materials. The preferred adsorbent comprises a selective zeolite commonly referred to as a molecular sieve. The preferred zeolites comprise synthetic crystalline aluminosilicates. Since the pure zeolites are relatively soft and powdery, the commercially-used molecular sieves comprise a binder such as clay or alumina to produce a stronger and more attrition-resistant adsorbent particle. The adsorbent particles preferably have a size range of about 20 to about 40 mesh (U.S.). The adsorbents which can be used in the process include the Type X or Type Y structured crystalline aluminosilicates or the naturally-occurring faujasite species. The Type X zeolite is described in U.S. Pat. No. 2,822,244 while the Type Y zeolite is described in U.S. Pat. No. 3,130,007. The adsorbents as described above can contain cations selected from the group consisting of alkali metals (Group I-A), the alkali-earth metals (Group II-A), the coinage metals (Group I-B), or the Group II-B metals. Preferred metals selected from the aforementioned group include lithium, sodium, potassium, magnesium, calcium, strontium, barium, copper, silver gold, zinc, cadmium, and mercury. Additionally, combinations of the above-mentioned metals may be included to enhance the adsorbent's selectivity for the olefins and to help reduce the harmful effects of side reactions including polymerization. It should be understood that the above mentioned adsorbents are not necessarily equivalent in terms of the increase in life to be expected as a result of removal of the aromatic by-products.

It is preferred to remove olefins from the adsorbent of the monoolefin adsorptive separation zone through the use of a liquid phase desorbent which is passed through the adsorbent bed. The desorbents which can be used in this process include olefinic-type hydrocarbons which boil at temperatures sufficiently different than the boiling temperature of the feedstock. Both branched chain or straight chain monoolefins can be used as desorbents. Additionally, aromatic-type hydrocarbons may be used as desorbents. In some instances, it will be advantageous to employ desorbents which contain a mixture of normal olefins or isoolefins and normal or isoparaffins or paraffins or aromatics. A typical desorbent which can be used for a feedstock containing $C_{10}$ to $C_{14}$ monoolefins and paraffins is a desorbent mixture comprising about 80 volume percent octene-1 and 20 volume percent isooctane. In most instances, it is preferred to use a lower molecular weight desorbent mixture as compared to the feedstock. An example of a desorbent which can be used when $C_6$ and $C_9$ feedstock being separated is a desorbent containing about 80 volume percent of a straight chain butylene and about 20 volume percent of normal butane.

Most separation methods do not perform perfect separation. In large scale commercial processes, it often becomes prohibitively costly to perform a complete recovery or separation of hydrocarbons. This is also true in the case of adsorptive recovery of olefins from the paraffin-olefin mixture. Recoveries of olefinic hydrocarbons can exceed 99 mole percent with the preferred simulated moving bed system, but the purity of the olefin product suffers as the recovery is increased. For this reason, most commercial process units are designed and operate to recover from 90 to about 95 mole percent of the olefins per pass. Therefore, about 5 to 10 mole percent of the original olefinic hydrocarbons will remain in the paraffinic recycle or monoolefin separation zone effluent stream which is passed into the dehydrogenation zone. This recycle stream will contain from about 0.5 to about 2.0 mole percent monoolefins in the subject process. This olefin concentration is significant due to its effect of deactivating the catalyst of the dehydrogenation zone in comparison to processes which recycle an olefin-free hydrocarbon stream to the dehydrogenation zone.

The recycle stream is preferably passed directly into the dehydrogenation zone as shown in the drawing. However, it must be realized that in commercial scale operations, process streams may be routed though storage facilities which serve to buffer flow rate differences between different process units. The recycle stream and other streams may therefore flow thorough tankage or surge drums within the integrated process. Other fractionation steps can also be employed within the overall process to remove undesired compounds, etc.

Referring now to FIG. 1, a feed stream comprising a mixture of $C_{10}$ to $C_{15}$ linear (straight chain) paraffins enters the process in a line 10 and is admixed with a recycle stream from a line 12, which comprises $C_{10}$ to $C_{15}$ paraffins and a minor amount of $C_{10}$ to $C_{15}$ monoolefins. The resultant reactor charge stream flows through a line 14 into a paraffin dehydrogenation zone 18 wherein in the presence of a solid catalyst some of the paraffins are converted to monoolefins. Diolefinic hydrocarbons, light hydrocarbons, and aromatic by-products are produced at a relatively small rate. A hydrogen-rich off-gas stream comprising the net hydrogen of the reaction is vented off via lines 16 and 24. A liquid phase stream comprising condensed $C_{10}$-plus hydrocarbons, of which about 15 mole percent are olefinic hydrocarbons and dissolved light hydrocarbons is passed through a line 20 into a selective diolefinic hydrogenation zone 26. Hydrogen from a line 22 is added to convert the diolefinic hydrocarbons to monoolefinic hydrocarbons.

A hydrogenation zone effluent stream is passed through a line 28 into a light ends stripping zone 30 wherein such materials as hydrogen, methane, ethane and, in this case, $C_9$-minus compounds are removed as the light gases in a line 36. The remaining $C_{10}$ to $C_{15}$ paraffins and olefinic hydrocarbons pass through a line 32 into a selective aromatics removal zone 34 wherein the aromatic by-products are removed by sorption onto a sorbent. An aromatics removal zone effluent stream is passed through a line 38 into a monoolefin separation zone 40 wherein over 90 mole percent of the olefinic hydrocarbons are concentrated into an olefinic rich product stream removed from the process in a line 42. The remaining paraffins and olefinic hydrocarbons are recycled through a line 12 as the recycle stream, which is referred to as the monoolefin separation zone effluent stream.

The beneficial operation of this invention will be further described in the context of an exemplified preferred embodiment which is the dehydrogenation of $C_{10}$ to $C_{15}$ paraffins to monoolefins and the recovery from the monoolefins of a stream rich in $C_{10}$ to $C_{15}$ monoolefins. The illustration of this invention in terms of a preferred embodiment is not meant to limit the claims of this invention to the particular details disclosed herein. The three examples presented herein are based on engineering calculations and actual operating experience with similar processes.

EXAMPLE 1

Example 1 illustrates the flow scheme in FIG. 1. 111.3 mass units of a feed stream consisting of paraffins is combined with 808.7 mass units of the separation zone effluent stream comprising 798.5 mass units of paraffins, 10.0 mass units of olefins including monoolefins and diolefins, and 0.2 mass units of aromatic by-products. The combined stream passes into the paraffin dehydrogenation zone 18. The dehydrogenation zone effluent stream passes through a diolefin hydrogenation zone 26 and a light ends stripping zone 30. 912.0 mass units of the stripped hydrogenation zone effluent stream comprising 802.9 mass units of paraffins, 105.4 mass units of olefins, and 3.7 mass units of aromatic by-products passes into the aromatics removal zone 34. The aromatics removal zone 34 removes 2.9 mass units of paraffins, 0.4 mass units of olefins, and 3.3 mass units of aromatic by-products. 905.4 mass units of the aromatics removal zone effluent stream comprising 800.0 mass units of paraffins, 105.0 mass units of olefins, and 0.4 mass units of aromatic by-products passes into the adsorptive separation zone 40. The monoolefin separation zone effluent stream is recovered from the adsorptive separation zone and recycled to the paraffin dehydrogenation zone 18. 96.7 mass units of the product stream comprising 1.5 mass units of paraffins, 95.0 mass units of olefins, and 0.2 mass units of aromatic by-products are recovered from the adsorptive separation zone and withdrawn from the process.

EXAMPLE 2

Figure 2:
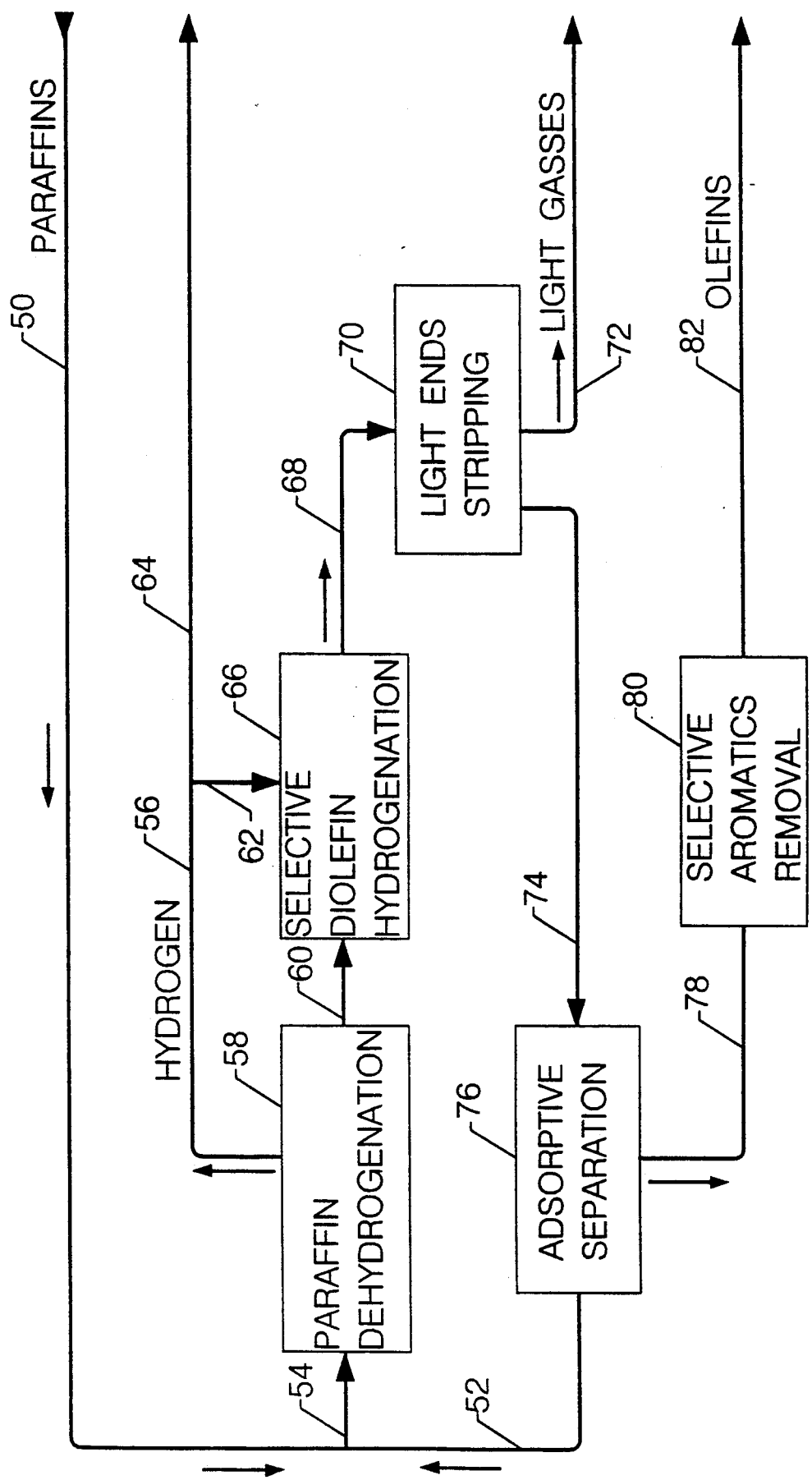
FIG. 2 is a simplified process flow diagram of a preferred embodiment of the invention where the aromatics removal zone is located downstream of the monoolefin adsorptive separation zone.

Example 2 illustrates a variation of the flow scheme in FIG. 2 in which the aromatics removal zone is located downstream of the adsorptive separation zone to remove aromatic by-products from the product stream. The stripped hydrogenation zone effluent stream passes directly from the light ends stripping zone to the adsorptive separation zone. 108.0 mass units of a feed stream consisting of paraffins is combined with 812.0 mass units of the monoolefin separation zone effluent stream comprising 798.5 mass units of paraffins, 10.0 mass units of olefins including monoolefins and diolefins, and 3.5 mass units of aromatic by-products. The combined stream passes into the paraffin dehydrogenation zone 58. The dehydrogenation zone effluent stream passes through a diolefin hydrogenation zone 66 and a light ends stripping zone 70. 912.0 mass units of the stripped hydrogenation zone effluent stream comprising 800.0 mass units of paraffins, 105.0 mass units of olefins, and 7.0 mass units of aromatic by-products passes into the adsorptive separation zone 76. The monoolefin separation zone effluent stream is recovered from the adsorptive separation zone and recycled to the paraffin dehydrogenation zone 58. 100.0 mass units of the product stream comprising 1.5 mass units of paraffins, 95.0 mass units of olefins, and 3.5 mass units of aromatic by-products are recovered from the adsorptive separation zone and passed into the aromatics removal zone 80. In a typical batch cyclic mode of operation, the aromatics removal zone 80 removes 3.0 mass units of olefins and 3.1 mass units of aromatic by-products, and thus 93.9 mass units of the aromatics removal zone effluent stream comprising 1.5 mass units of paraffins, 92.0 mass units of olefins, and 0.4 mass units of aromatic by-products is withdrawn from the process. Alternatively, in a typical continuous cyclic mode of operation, the aromatics removal zone 80 removes 0.5 mass units of olefins and 3.3 mass units of aromatic by-products, and thus 96.2 mass units of the aromatics removal zone effluent stream comprising 1.5 mass units of paraffins, 94.5 mass units of olefins, and 0.2 mass units of aromatic by-products is withdrawn from the process.

EXAMPLE 3

Example 3 illustrates a variation of the flow scheme in FIG. 1 that is without the benefit of the present invention and that is without an aromatics removal zone. The stripped hydrogenation zone effluent stream passes directly from the light ends stripping zone to the adsorptive separation zone. 108.0 mass units of a feed stream consisting of paraffins is combined with 812.0 mass units of the monoolefin separation zone effluent stream comprising 798.5 mass units of paraffins, 10.0 mass units of olefins including monoolefins and diolefins, and 3.5 mass units of aromatic by-products. The combined stream passes into the paraffin dehydrogenation zone. The dehydrogenation zone effluent stream passes through a diolefin hydrogenation zone and a light ends stripping zone. 912.0 mass units of the stripped hydrogenation zone effluent stream comprising 800.0 mass units of paraffins, 105.0 mass units of olefins, and 7.0 mass units of aromatic by-products passes into the adsorptive separation zone. The monoolefin separation zone effluent stream is recovered from the adsorptive separation zone and recycled to the paraffin dehydrogenation zone. 100.0 mass units of the product stream comprising 1.5 mass units of paraffins, 95.0 mass units of olefins, and 3.5 mass units of aromatic by-products are recovered from the adsorptive separation zone and withdrawn from the process.

What is claimed is:

1. In a process for the production of monoolefinic hydrocarbons by:
   (a) passing a feed stream comprising at least one $C_4$ to $C_{20}$ feed paraffinic hydrocarbon into a dehydrogenation zone to dehydrogenate the entering feed paraffinic hydrocarbon to a monoolefinic hydrocarbon and recovering therefrom a dehydrogenation zone effluent stream comprising light hydrocarbons, aromatic by-products, feed paraffinic hydrocarbons, and monoolefinic hydrocarbons corresponding in carbon number to said feed paraffinic hydrocarbon;
   (b) passing said dehydrogenation zone effluent stream into a stripping zone to strip the entering light hydrocarbons from said dehydrogenation zone effluent stream and recovering therefrom a stripped dehydrogenation zone effluent stream comprising feed paraffinic hydrocarbons and monoolefinic hydrocarbons;
   (c) passing said stripped dehydrogenation zone effluent stream into a monoolefinic separation zone to concentrate the entering monoolefinic hydrocarbons and recovering therefrom a product stream having a first concentration of monoolefinic hydrocarbon and a monoolefin separation zone effluent stream having a second concentration of monoolefinic hydrocarbon that is less than said first concentration;
   (d) recycling at least a portion of said monoolefin separation zone effluent stream to said dehydrogenation zone; and
   (e) withdrawing said product stream from said process;
   the improvement comprising selectively removing at least a portion of said aromatic by-products from at least one of said dehydrogenation zone effluent stream, said stripped dehydrogenation zone effluent stream, and said monoolefin separation zone effluent stream in at least one aromatics removal zone and thereby reducing the concentration of aromatic by-products in said stripped dehydrogenation zone effluent stream to a level no more than about 0.5 weight percent.

2. The process of claim 1 further characterized in that said feed stream comprises feed paraffinic hydrocarbons having two different carbon numbers.

3. The process of claim 1 wherein said concentration of aromatic by-products in said stripped dehydrogenation zone effluent stream is less than about 0.2 weight percent.

4. The process of claim 3 wherein said concentration of aromatic by-products in said stripped dehydrogenation zone effluent stream is less than about 0.1 weight percent.

5. The process of claim 1 further characterized in that said aromatics removal zone is an aromatics sorptive separation zone or a liquid-liquid extraction zone.

6. The process of claim 5 further characterized in that said aromatics sorptive separation zone contains at least one member of the group consisting of activated carbon, silica, activated alumina, activated charcoal, silica-alumina, clay, silica gel, cellulose acetate, synthetic magnesium silicate, macroporous magnesium silicate, macroporous polystyrene gel, and a molecular sieve.

7. The process of claim 6 wherein said aromatics sorptive separation zone contains a molecular sieve.

8. The process of claim 7 further characterized in that said molecular sieve is 13×zeolite.

9. The process of claim 6 further characterized in that said aromatics removal zone operates at a temperature of from about 20° to about 300° C.

10. The process of claim 6 further characterized in that said aromatics removal zone operates at a liquid hourly space velocity of from about 1 to about 10 $hr^{-1}$.

11. The process of claim 1 further characterized in that said dehydrogenation zone effluent stream comprises diolefinic hydrocarbons corresponding to said feed paraffinic hydrocarbon and at least a portion of said dehydrogenation zone effluent stream passes into a selective hydrogenation zone to convert the entering diolefinic hydrocarbons to monoolefinic hydrocarbons prior to passing to said stripping zone.

12. The process of claim 11 further characterized in that said aromatics sorptive separation zone and at least one of said dehydrogenation zone, said selective hydrogenation zone, and said monoolefin separation zone are contained in a common vessel.

13. The process of claim 5 further characterized in that said liquid-liquid extraction zone contains a sulfolane.

14. The process of claim 1 further characterized in that said aromatics removal zone maintains in a liquid phase said aromatic by-products in the stream from which said aromatic by-products are selectively removed.

15. The process of claim 1 further characterized in that said monoolefin separation zone comprises a fixed bed of a solid adsorbent which selectively adsorbs at least one of olefinic hydrocarbons and paraffinic hydrocarbons.

16. The process of claim 1 further characterized in that all of said monoolefin separation zone effluent stream is passed into said dehydrogenation zone.

17. The process of claim 1 further characterized in that said second concentration is from about 0.5 to about 2.0 weight percent monoolefinic hydrocarbon.

18. A process for the production of monoolefinic hydrocarbons comprising:
(a) passing a feed stream comprising at least one $C_4$ to $C_{20}$ feed paraffinic hydrocarbon into a dehydrogenation zone to dehydrogenate the entering feed paraffinic hydrocarbon to a monoolefinic hydrocarbon and recovering therefrom a dehydrogenation zone effluent stream comprising light hydrocarbons, aromatic by-products, feed paraffinic hydrocarbons, and monoolefinic hydrocarbons corresponding in carbon number to said feed paraffinic hydrocarbon;
(b) passing said hydrogenation zone effluent stream into a stripping zone to strip the entering light hydrocarbons from said dehydrogenation zone effluent stream and recovering therefrom a stripped dehydrogenation zone effluent stream comprising feed paraffinic hydrocarbons, aromatic by-products, and monoolefinic hydrocarbons;
(c) passing said stripped dehydrogenation zone effluent stream into a monoolefin separation zone to concentrate the entering monoolefinic hydrocarbons and recovering therefrom a product stream having a first concentration of monoolefinic hydrocarbon and a monoolefin separation zone effluent stream having a second concentration of monoolefinic hydrocarbon that is less than said first concentration;
(d) recycling at least a portion of said monoolefin separation zone effluent stream to said dehydrogenation zone;
(e) passing said product stream into at least one aromatics sorptive separation zone containing a sorbent to selectively remove at least a portion of said aromatic by-products from said product stream and recovering therefrom an aromatics sorptive separation zone effluent stream having a concentration of aromatic by-products no more than about 0.5 weight percent;
(f) withdrawing said aromatics sorptive separation zone effluent stream from said process;
(g) regenerating said sorbent by contacting said sorbent and a regenerant stream comprising benzene at regeneration conditions effective to desorb aromatic by-products from said sorbent and produce a regeneration effluent stream comprising benzene and monolefinic hydrocarbons; and
(h) passing at least a portion of said regenerant effluent stream into a regenerant separation zone to separate the entering hydrocarbons into a first stream comprising benzene and a second stream comprising said monolefinic hydrocarbons; and
(i) forming at least a portion of said regenerant stream from at least a portion of said first stream.

19. The process of claim 18 further characterized in that said dehydrogenation zone effluent stream comprises diolefinic hydrocarbons corresponding to said feed paraffinic hydrocarbon and at least a portion of said dehydrogenation zone effluent stream passes into a selective hydrogenation zone to convert the entering diolefinic hydrocarbons to monoolefinic hydrocarbons prior to passing to said stripping zone.

20. The process of claim 18 further characterized in that said aromatics sorptive separation zone contains at least one member of the group consisting of activated carbon, silica, activated alumina, activated charcoal, silica-alumina, clay, silica gel, cellulose acetate, synthetic magnesium silicate, macroporous magnesium silicate, macroporous polystyrene gel, and a molecular sieve.

21. The process of claim 20 wherein said aromatics sorptive separation zone contains a molecular sieve.

22. The process of claim 21 further characterized in that said molecular sieve is $13 \times$ zeolite.

23. A process for the production of monoolefinic hydrocarbons comprising:
(a) passing a feed stream comprising at least two different $C_6$-plus feed paraffinic hydrocarbons into a catalytic paraffin dehydrogenation zone to dehydrogenate the entering feed paraffinic hydrocarbons to monoolefinic hydrocarbons and recovering therefrom a hydrogen-rich gas stream and a liquid-phase effluent stream which comprises light hydrocarbons, aromatic by-products, feed paraffinic hydrocarbons and monoolefinic and diolefinic hydrocarbons corresponding in carbon number to said feed paraffinic hydrocarbons;
(b) passing said liquid-phase effluent stream into a selective hydrogenation zone to convert the entering diolefinic hydrocarbons to monoolefinic hydrocarbons and recovering therefrom a selective hydrogenation zone effluent stream comprising light hydrocarbons, aromatic by-products, feed paraffinic hydrocarbons and monoolefinic hydrocarbons;
(c) passing said selective hydrogenation zone effluent stream into a fractionation zone to remove the entering dissolved hydrogen and said light hydrocarbons from said selective hydrogenation zone effluent stream and recovering therefrom a stripped selective hydrogenation zone effluent stream comprising feed paraffinic hydrocarbons and monoolefinic hydrocarbons;
(d) passing said stripped selective hydrogenation zone effluent stream into at least one aromatics removal zone comprising a $13 \times$ zeolite sorbent at removal conditions including a temperature of from about 20° to about 300° C. and a liquid hourly space velocity of from about 1 to about 10 $hr^{-1}$ to selectively remove said aromatic by-products from said stripped selective hydrogenation zone effluent stream and reduce the concentration of aromatic by-products in said stripped selective hydrogenation zone effluent stream to a level no more than about 0.5 weight percent and recovering therefrom an aromatics removal zone effluent stream comprising feed paraffinic hydrocarbons and monoolefinic hydrocarbons;
(e) contacting said aromatics removal zone effluent stream with a solid adsorbent in a monoolefin adsorptive separation zone to separate the entering monoolefinic hydrocarbons into a product stream and a monoolefin separation zone effluent stream having a concentration of monoolefinic hydrocarbons from about 0.5 to about 2.0 weight percent;
(f) recycling said monoolefin separation zone effluent stream to said dehydrogenation zone; and
(g) withdrawing said product stream from said process.

* * * * *